US008470380B2

(12) United States Patent
Wood et al.

(10) Patent No.: US 8,470,380 B2
(45) Date of Patent: Jun. 25, 2013

(54) POLYPHENOL EXTRACTION PROCESS

(75) Inventors: Richard Wood, Herefordshire (GB); Paul Kroon, Norwich (GB); Ricky Lee Green, Roecliffe (GB)

(73) Assignee: Coressence Limited, Herefordshire (GB)

( * ) Notice: Subject to any disclaimer, the term of this patent is extended or adjusted under 35 U.S.C. 154(b) by 578 days.

(21) Appl. No.: 12/376,769

(22) PCT Filed: Aug. 8, 2007

(86) PCT No.: PCT/GB2007/003021
§ 371 (c)(1),
(2), (4) Date: Sep. 7, 2010

(87) PCT Pub. No.: WO2008/017842
PCT Pub. Date: Feb. 14, 2008

(65) Prior Publication Data
US 2010/0331399 A1 Dec. 30, 2010

(30) Foreign Application Priority Data
Aug. 9, 2006 (GB) .................................. 0615781.2

(51) Int. Cl.
*A61K 36/00* (2006.01)
(52) U.S. Cl.
USPC ............................ 424/769; 424/777; 424/725
(58) Field of Classification Search
None
See application file for complete search history.

(56) References Cited

U.S. PATENT DOCUMENTS

| | | | |
|---|---|---|---|
| 5,912,363 A | 6/1999 | Nafisi-Movaghar et al. | |
| 5,994,413 A * | 11/1999 | Tanabe et al. | 514/732 |
| 6,509,054 B1 * | 1/2003 | Haddad et al. | 426/615 |
| 6,824,797 B2 * | 11/2004 | Goupy et al. | 424/764 |
| 2004/0014805 A1 | 1/2004 | Shoji et al. | |
| 2004/0156925 A1 | 8/2004 | Howell et al. | |
| 2006/0165609 A1 * | 7/2006 | Inaba et al. | 424/49 |
| 2008/0254153 A1 * | 10/2008 | Wang et al. | 424/729 |
| 2011/0135770 A1 | 6/2011 | Wood et al. | |

FOREIGN PATENT DOCUMENTS

| | | |
|---|---|---|
| DE | 2061480 | 6/1972 |
| DE | 19823679 | 11/1999 |
| EP | 0412300 | 2/1991 |
| EP | 0657169 | 6/1995 |
| EP | 1 525 887 A1 | 4/2005 |
| WO | WO 96/24327 | 8/1996 |
| WO | WO 98/41096 | 9/1998 |
| WO | WO-2007/026101 A1 | 3/2007 |

OTHER PUBLICATIONS

Renard et al. Intl. J. Biological Macromolecules. 2001. vol. 29, pp. 115-125.*
Guyot et al. J. Agric. Food Chem. 1998. vol. 46, pp. 1698-1705.*
Alonso-Salces et al. Food Chem. 2005. vol. 93, pp. 113-123.*
Alonso-Salces et al. J. Chromatography A. 2001. vol. 933, pp. 37-43.*
Tsanova-Savova, S. Dokladi na B"Igarskata Akademiya na Naukite. 2003. vol. 56, No. 8, pp. 97-100.*
Graziani et al. Gut. 2005. vol. 54, pp. 193-200.*
Risch et al. Z. Lebensm Unters Forsch. 1988. vol. 186, pp. 225-230.*
Guyot et al. Phytochem. 1997. vol. 44, No. 2, pp. 351-357.*
Arts et al., "Dietary catechins in relation to coronary heart disease death among postmenopausal women." (2001) Epidemiology 12(6): 668-675.
Gu et al. "Concentrations of proanthocyanidins in common foods and estimations of normal consumption." (2004) *J. Nutr* 134(3): 613-7.
Guyot et al., "Variability of the polyphenolic composition of cider apple (*Malus domestica*) fruits and juices." (2003) *J Agric Food Chem.* 51, 6240-6247.
Heptinstall et al., "Cocoa flavanols and platelet and leukocyte function: recent in vitro and ex vivo studies in healthy adults." (2006) *J Cardiovasc Pharmacol* 47 Suppl 2: S197-205.
Keen et al., "Cocoa antioxidants and cardiovascular health." (2005) Am. J. Clin. Nutr. 81 (1 Suppl) : 298S-303S.
Leal et al. " Economic burden of cardiovascular diseases in the enlarged European Union." (2006) Eur.Heart J. 27(13):1610-9.
Lu et al., "Identification and quantification of major polyphenols in apple pomace." (1997) Food Chemistry, vol. 59, No. 2, 187-194.
Mink et al., "Flavanoid intake and cardiovascular disease mortality: a prospective study in postmenopausal women." (2007) Am J Clin Nutr. 85(3): 895-909.
Prior et al. , "Occurrence and biological significance of proanthocyanidins in the American diet." (2005) Phytochemistry 66(18): 2264-80).
Rios et al., "Cocoa procyanidins are stable during gastric transit in humans." (2002) *Am. J. Clin. Nutr.*, 76, 1106-1110.
Seeram et al. "Cyclooxygenase inhibitory and antioxidant compounds from crabapple fruits." (2003) J. Agricultural and Food Chemistry, vol. 51 No. 7 1948-1951.
Sesso et al., "Flavanoid intake and the risk of cardiovascular disease in women." (2003) Am J Clin Nutr. 77, 1400-1408.
Svedstrom et al. "High-performance liquid chromatographic determination of oligomeric procyanidins form dimmers up to the hexamer in hawthorn." (2002) J. Chromatography vol. 968, No. 1-2, 53-60.
Vita J., "Polyphenols and cardiovascular disease: effects on endothelial and platelet function." (2005) Am. J Clin. Nutr. 81 (I. 20 Suppl), 292S-297S.
Gorinstein et al. (2001), "Comparative contents of dietary fiber, total phenolics and minerals in persimmons and apples," J. Agric. Food Chem. 49:952-957.
Lachman et al. (2006), "Polyphenol content and antiradical activity in different apple varieties," Hort, Sci 33(3):95-102.
Linn et al. (2004), "Postzygotic isolating factor in sympatric speciation in Rhagoletis files: reduced response of hybrids to parental host-fruit odors," Proc. Natl. Acad. Sci. 101(51):17753-17758.
International Search Report for International Patent Application No. PCT/GB2007/003021, dated Dec. 21, 2007.
International Search Report for International Patent Application No. PCT/GB2007/003025, dated Dec. 21, 2007.
Restriction Requirement for U.S. Appl. No. 12/376,770, dated Jun. 25, 2012.
Office Action for U.S. Appl. No. 12/376,770, dated Aug. 7, 2012.

* cited by examiner

*Primary Examiner* — Chris R Tate
(74) *Attorney, Agent, or Firm* — Foley & Lardner LLP; Antoinette F. Konski; Photon Rao

(57) ABSTRACT

The invention relates to a process for extracting one or more polyphenols from fruits such as apples and to uses of said extracts in the treatment or prophylaxis of cardiovascular disease, colon cancer and digestive health.

9 Claims, 10 Drawing Sheets

POLYPHENOL EXTRACTION PROCESS

The invention relates to a process for extracting one or more polyphenols from fruits such as apples and to uses of said extracts in the treatment or prophylaxis of cardiovascular disease, colon cancer and digestive health.

Cardiovascular disease (CVD) and cancer are two leading causes of death worldwide.

In the European Union, CVD is the main source of morbidity and mortality, costing 169 billion Euros annually (Leal et al. (2006) Eur. Heart J. 27(13): 1610-9), whilst in the US, the American Heart Association has estimated that 71,300,000 Americans have one or more forms of CVD.

According to the World Health Organisation, cancer kills about 7.6 million (or 13%) people worldwide every year. In particular, cancers of the lung, stomach, liver, colon and breast are responsible for over half these deaths.

Epidemiological evidence seems to suggest that a diet high in fruits and vegetables offers a significant protective effect against these chronic diseases.

Much of this protective effect has been attributed to a major class of phytochemicals found commonly in fruits and vegetables called polyphenols.

Polyphenols have been referred to as nature's biological response modifiers because of strong experimental evidence demonstrating their ability to modify the body's reaction to allergens, viruses, and carcinogens. They show anti-allergic, anti-inflammatory, anti-microbial and anti-cancer activity. In addition, polyphenols act as powerful antioxidants, protecting against oxidative and free radical damage, and help to prevent various diseases associated with oxidative stress.

However, it has been estimated that most people do not consume sufficient quantities to obtain the health benefits offered by polyphenols. For example, the average current US daily intake of epicatechin is 2 to 4 times lower than the projected dose required to achieve a CVD risk reduction (Gu et al. (2004) J Nutr 134(3): 613-7; Prior and Gu (2005) Phytochemistry 66(18): 2264-80). As a result, increasing intake through the diet has emerged as an important health goal.

Apples can be a significant source of polyphenols, providing approximately 10% of the projected dose required to achieve a CVD risk reduction (Gu et al. (2004) supra). However, the concentration and distribution of polyphenols varies dramatically in each variety (see Table 1). Indeed, many modern dessert apples can have a polyphenol content less than 1000 mg/kg.

Furthermore, processing of apples has been found to affect the polyphenolic content. For example, as much as 95% of the total polyphenols may remain in the pomace when apple juice is extracted. More importantly, procyanidins have the lowest yield in the juice (32%) (Guyot and Marnet (2003) J. Agric. Food Chem. 51(21), 6240-6247).

It is therefore an object of this invention to provide an improved process for isolating polyphenols from fruits such as apples.

According to a first aspect of the invention, there is provided a process for extracting one or more polyphenols from a fruit which comprises the steps of:
(a) removing the coating of the fruit;
(b) freeze-drying or freezing the fruit obtained in step (a);
(c) optionally powdering the freeze-dried or frozen material obtained in step (b);
(d) subjecting the material obtained in step (b) or step (c) to one or more solvent extraction cycles;
and optionally thereafter
(e) isolating one or more polyphenols from the liquid extract obtained in step (d).

In one embodiment of the invention, there is provided a process for preparing a polyphenol-containing fraction from an apple which comprises the steps of:
(a) removing the natural wax coating of the apple;
(b) freeze-drying or freezing the apple obtained in step (a); and optionally thereafter
(c) powdering the freeze-dried or frozen material obtained in step (b).

In a further embodiment of the invention, there is provided a process for isolating one or more polyphenols from an apple which comprises the steps of:
(a) removing the natural wax coating of the apple;
(b) freeze-drying or freezing the apple obtained in step (a);
(c) powdering the freeze-dried or frozen material obtained in step (b);
(d) subjecting the powdered material obtained in step (c) to one or more solvent extraction cycles;
and optionally thereafter
(e) centrifuging the liquid extract obtained in step (d).

In one embodiment, the fruit is an apple. In a further embodiment, the fruit is a "red-cut through" apple. It will be appreciated that the term "red-cut through" is well known in the art and refers to an apple having red flesh.

When used herein, the term polyphenol refers to a group of chemicals characterised by the presence of more than one phenol group per molecule. In one embodiment, the polyphenols include the sub-group flavonoids.

Over 5000 naturally occurring flavonoids have been characterised from various plants. They have been classified according to their chemical structure and can be categorised into various sub-classes. In one embodiment, the flavonoids include:

(a) flavanones (e.g. Hesperetin, Naringenin, Eriodictyol), which use the chemical skeleton shown in formula (I):

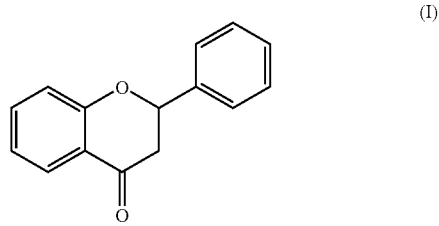 [SMILES: O=C1CC(c2ccccc2)Oc2ccccc21]

(I)

(b) isoflavanones (e.g. Genistein, Daidzein, Glycitein), which use the chemical skeleton shown in formula (II):

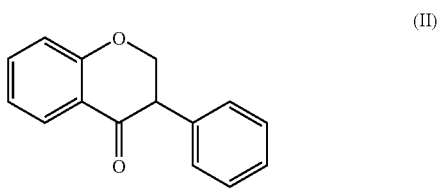 [SMILES: O=C1c2ccccc2OCC1c1ccccc1]

(II)

(c) flavones (e.g. Luteolin, Apigenin, Tangeritin), which use the chemical skeleton shown in formula (III):

(III)

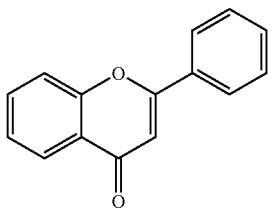

(d) flavanols (e.g. Quercetin, Kaempferol, Myricetin, Isorhamnetin, Pachypodol, Rhamnazin), which use the chemical skeleton shown in formula (IV):

(IV)

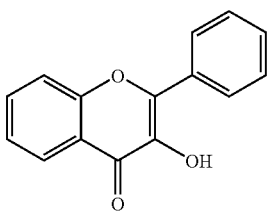

(e) flavan-3-ols (e.g. Catechin, Gallocatechin, Epicatechin, Epigallocatechin), which use the chemical skeleton shown in formula (V):

(V)

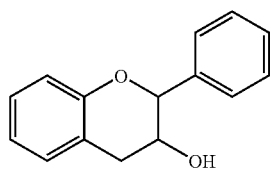

flavan-3,4-diol, which use the chemical skeleton shown in formula (VI):

(VI)

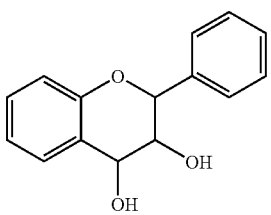

(g) dihydroflavonols, which use the chemical skeleton shown in formula (VII):

(VII)

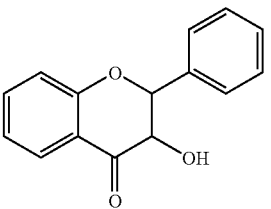

(h) anthocyanidins (e.g. Cyanidin, Delphinidin, Malvinidin, Pelargonidin, Peonidin, Petunidin), which use the chemical skeleton shown in formula (VIII):

(VIII)

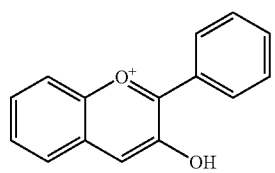

(i) anthocyanins, which use the chemical skeleton shown in formula (IX):

(IX)

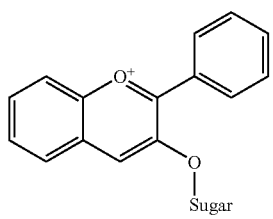

wherein sugar may be selected from glucose, arabinose, galactose or the like.

In one embodiment, the flavonoids include proanthocyanidins. Proanthocyanidins are biopolymers composed of flavan-3-ol subunits. Polymers are linked principally through the 4 and 8 positions and 4 and 6 positions. In a further embodiment, the proanthocyanidin is a 4,8 linked polymer, having the structure shown in Formula (X):

(X)

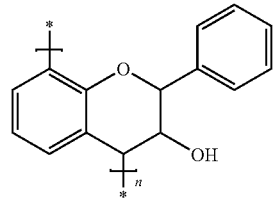

In one embodiment, the flavonoids include anthocyanidins, proanthocyanidins, flavanols, flavanols, flavones, flavanones and isoflavones. In a further embodiment, the flavonoids include flavanols and proanthocyanidins.

In one embodiment, the flavan-3-ols have the structure shown in formula (V)a:

(V)a

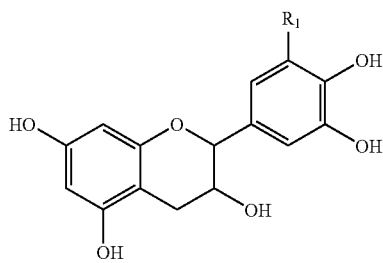

wherein $R^1$ represents hydrogen or an OH group.

In one embodiment, the flavan-3-ols have the structure shown in formula (V)b:

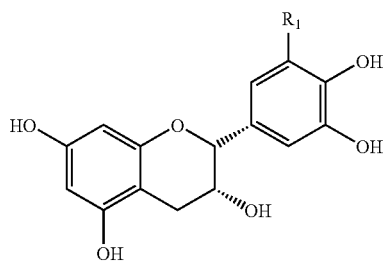

(V)b wherein R¹ is as defined above.

Compounds of formula (V)b wherein R¹ represents hydrogen are known as epicatechin and compounds of formula (V)b wherein R¹ represents an OH group are known as epigallocatechin.

In one embodiment, the flavan-3-ols have the structure shown in formula (V)c:

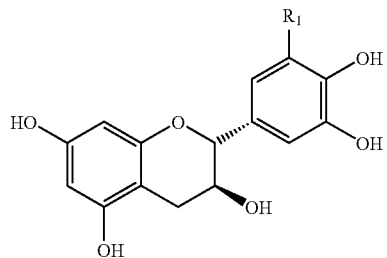

(V)c wherein R¹ is as defined above.

Compounds of formula (V)c wherein R¹ represents hydrogen are known as catechin and compounds of formula (V)c wherein R¹ represents an OH group are known as gallocatechin.

In one embodiment, the anthocyanidins include cyanidin, having the structure shown in formula (VIII) a:

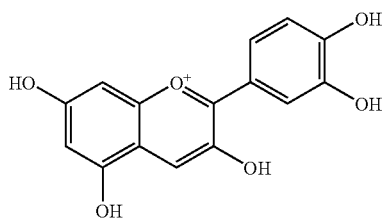

(VIII)a

In one embodiment, the flavonoids include delphinidin, having the structure shown in formula (VIII)b:

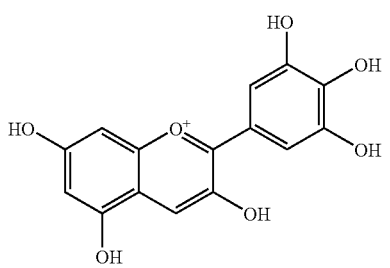

(VIII)b

In one embodiment, the proanthocyanidins have the structure shown in formula (X)a:

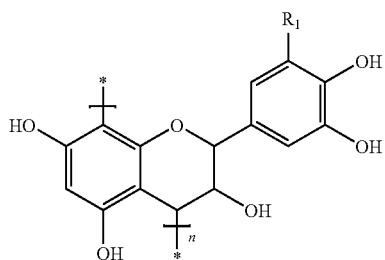

(X)a wherein R¹ is as defined above; and
n=2 to 30.

In one embodiment, n>10 (i.e. 11-30). In a further embodiment, the compounds of formula (IV) have a molecular weight in excess of 1000. In a yet further embodiment, the compounds of formula (IV) have a molecular weight >1000 and <9000 (e.g. >3000 and <9000).

Proanthocyanidins include the subgroups of procyanidins and prodelphinidins and upon acid hydrolysis these yield cyanidin and delphinidin respectively.

In one embodiment, the one or more polyphenols extracted by the process of the invention comprise epicatechin (i.e. a compound of formula (V)b wherein R¹ represents hydrogen).

Removal of the coating of the fruit in step (a) (e.g. removal of the natural wax coating of an apple) advantageously reduces foaming during the subsequent solvent extraction cycles in step (d). In one embodiment, the removal comprises a washing step using a suitable solvent, such as ethanol, methanol or acetone. The natural wax can then be recovered from the resultant wax/solvent extraction mixture by distillation which can advantageously be used as a raw material for cosmetic products.

It will be appreciated that the freeze-drying or freezing step (b) typically comprises procedures known to those skilled in the art. For example, freeze-drying will involve pre-frozen whole apples of less than 25 mm in diameter at −18° C. being dried under vacuum, ensuring that the water is removed as vapour. This step advantageously preserves the overall product structure and size as well as maintaining the integrity of the resultant polyphenols.

An advantage provided by the frozen samples is the production of ice crystals which rupture cellular structure and ensure easier release of polyphenols. Thus, freezing improves the extraction process efficiency. In addition, freeze-drying enhances the availability of catechin and epicatechin molecules, when compared with other drying methods such as oven, air or thermal drying.

The powdering step (c) comprises procedures known to those skilled in the art. For example, powdering on a small scale may be conducted in a conventional food processor. Large scale powdering techniques may suitably be employed in an analogous manner and will generally require exclusion of moist air to prevent re-hydration (e.g. by use of an inert atmosphere, such as a nitrogen blanket or by purging). Powdering prevents oxidation (e.g. by polyphenol oxidase) which would result in a degradation of polyphenols and also provides small sized particles which results in enhancement of the subsequent extraction phase. In a further embodiment, powdering is carried out in the presence of liquid nitrogen, which prevents the material from macerating during the subsequent extraction cycle in step (d). The powdered apples obtained in step (c) are generally of a particle size that is beneficial for the subsequent solvent extraction cycle, suitably between 1 and 25 mm. This aspect of the invention provides the significant advantage of not requiring enzyme processing which causes degradation of the polyphenols.

The extraction cycle in step (d) typically occurs in a continuous horizontal counter current extractor, or a batch extractor (with solvent extraction and multi-solvent extraction and downstream solvent recovery), or a counter current vertical column extractor (with downstream liquid to liquid extraction centrifuges with wiped film evaporators) or a semi-continuous rotary drum vacuum filter of suitable design or a centrifugal decanter. It will be appreciated that a counter current extractor is well known to those skilled in the art and could either be a continuous or batch counter current extractor.

Step (d) typically comprises one or more extracting solvents including methanol, ethanol, water, acetone and any mixture thereof. These solvents help to denature plant enzymes and therefore eliminate problems of residual enzyme activity.

In one embodiment, the extracting solvent is water. In a further embodiment, the water may be distilled, deionised, deaerated and heated to a temperature between 65° C. and 80° C. (e.g. between 70° C. and 75° C., such as between 73° C. and 75° C.). The use of water as an extracting solvent provides substantial advantages, for example, it can be used directly in the resultant foodstuff without removal and it has no environmental impact unlike other solvents. The use of deaerated water provides the advantage of inhibiting oxidases which would normally cause degradation of the resultant polyphenols (reducing polyphenol yields by up to 50%). Previous approaches to this problem have incorporated specific agents to inhibit oxidases (e.g. ascorbic acid) however this approach is of limited success because the oxidases are only suppressed and not eliminated and furthermore the agents may require removal prior to downstream use (e.g. in foodstuffs). The use of heated water above 70° C. provides the advantage of simultaneously pasteurising the extract (pasteurisation occurs above 73° C.) and extracting 95% of polyphenols in a single cycle.

In one embodiment, the water is used in the solvent extraction step at a pressure greater than 1 bar (e.g. 2-5 bar, such as 4 bar). The provision of water under high pressure provides the advantage of overcoming the back pressures associated with the extraction process.

In one embodiment, the extracting solvent is methanol which advantageously is capable of extracting 95% of polyphenols in a single cycle.

In an alternative embodiment, the extracting solvent is acetone which is a more environmentally acceptable solvent than methanol.

In one embodiment, the extraction cycle (d) comprises a plurality of separate stages, suitably three stages.

In one embodiment, the first stage of the solvent extraction cycle makes use of an extracting solvent comprising 50 to 100% methanol and 0 to 50% water, suitably 60 to 90% methanol and 10 to 40% water, for example 80% methanol and 20% water. This stage helps to extract the residual catechin and epicatechin molecules from the powdered apples obtained in step (c).

In one embodiment, the powdered apples are hydrolysed prior to the first stage, which breaks glycoside bonds. The hydrolysis step is not necessary for low molecular weight polyphenols because these materials exist exclusively as non-sugar bonded polyphenols.

In one embodiment, a second stage of the solvent extraction cycle makes use of a solvent comprising 0 to 75% ethanol and 25 to 100% water, suitably 40 to 60% ethanol and 40 to 60% water, for example 50% ethanol and 50% water. This stage assists in recovering the higher molecular weight oligomers and polymers from the apple biomass.

In one embodiment, the second stage of the extraction cycle can be preceded by a water wash. For example, the extraction biomass may typically be washed in a counter current extractor with water to swell the material as a pre-stage in advance of further stage extraction. This stage advantageously increases the extraction availability of polymers.

In one embodiment, a third stage of the extraction cycle makes use of an extracting solvent comprising 50 to 100% acetone and 0 to 50% water, suitably 60 to 80% methanol and 20 to 40% water, for example 70% acetone and 30% water.

In an alternative embodiment, the extraction cycle can comprise one continuous stage. In this case, the extraction cycle can be arranged to sequentially apply a combination of extracting solvents. As a result, the extraction sequence is: 80% methanol, 20% water, 50% methanol 50% water and 75% acetone 25% water. The continuous arrangement is beneficially more appropriate for large scale biomass throughout when compared with the batch extraction which is more suitable for smaller biomass throughput and trial quantities.

The solvent extraction cycle produces an extraction liquid and a soluble apple pulp. In one embodiment, the solvent extraction cycle is repeated, suitably three times. In a further embodiment, the soluble apple pulp may be recovered from the extraction process, dried, by methods well known to those skilled in the art, e.g. spray drying, thermal drying, freeze drying, etc. and packed as dehydrated apple fibre, suitably in heat sealed aluminium foil bags or containers.

In one embodiment, the isolation step (e) comprises centrifugation in accordance with procedures known to those skilled in the art. In one embodiment, the extraction liquid is centrifuged for 15 to 30 minutes at 3000 to 9000 g. This helps to separate any remaining solid apple pulp from extraction liquid and eliminates the bulk biomass material prior to the subsequent filtration step.

In one embodiment, the supernatant obtained by centrifugation is subjected to ultra-filtration. This provides the advantage of selectively filtering out polyphenols of differing molecular weights.

In one embodiment, low molecular weight polyphenols are separated, e.g. molecules with a molecular weight of less than 600. This embodiment creates a filtrate comprising solvent, polyphenol monomers, e.g. epicatechin and catechin (molecular weight=290), polyphenol dimers (molecular weight=580), monosaccharides and disaccharides, e.g. fructose and sucrose (molecular weight=342).

In an alternative embodiment, molecules with a molecular weight of less than 300 are separated which creates a filtrate comprising solvent and polyphenol monomers, e.g. epicatechin and catechin (molecular weight of 290).

In one embodiment, the residual solvent may be removed e.g. either by a single or multi-stage evaporation step in the presence of an inert gas (e.g. nitrogen) and recovered by condensation for recycling. In a further embodiment, the solvent is washed with ethyl acetate to ensure that monomers and dimers remain in the water phase solution for post processing prior to the final separation stage.

Therefore, the process results in two isolates, each in aqueous solution. In one embodiment, the first isolate comprises low molecular weight polyphenols, and the second isolate comprises high molecular weight polyphenols, e.g. molecules with a molecular weight of more than 600.

In a further embodiment, the isolates are both dried under vacuum at a temperature less than 30° C., e.g. less than 20° C. and optionally freeze-dried.

In one embodiment, there is provided a process for isolating one or more polyphenols from an apple which comprises the steps of:

(a) removing the natural wax coating of the apple;
(b) freeze-drying or freezing the apple obtained in step (a);
(c) powdering the freeze-dried or frozen material obtained in step (b);
(d) subjecting the material obtained in step (c) to one or more solvent extraction cycles wherein the solvent is water;
(e) evaporation of the water from step (d);
(f) chromatographic separation of isolated polyphenols from the crude extract prepared from step (e) by elution with ethanol;
(g) evaporation of ethanol to yield the isolated polyphenols.

According to a second aspect of the invention there is provided a polyphenol containing extract obtainable by the process as hereinbefore described.

It has been found that extraction of polyphenols from red-cut through apples in accordance with the process of the invention results in a rich red coloured extract having a high proportion of polyphenols (e.g. greater than 18% epicatechin). It is believed that the polyphenols within the extract have been fixed as anthocyanidins which are a recognised food colourant (cyanidin; E163a). This food colourant has been approved for use in levels of 2.5 mg/kg body weight and the process of the invention provides cyanidin in a concentration of 1 mg/kg body weight. Thus, in one embodiment, there is provided a natural food colourant which comprises the polyphenol containing extract of the invention. The use of the polyphenol extract as a food colouring provides two significant advantages, safe colouration of food and the provision of high levels of beneficial polyphenols.

Methods of Treatment

Polyphenols have been demonstrated to show numerous health benefits. For example, epidemiological studies have suggested that higher flavonoid intake is associated with a decreased risk of CVD, (Arts et al (2001) Epidemiology 12(6): 668-675; Sesso et al. Am J Clin Nutr 77: 1400-8; Mink et al. (2007) Am J Clin Nutr 85(3): 895-909), which may be a result of their ability to improve endothelial function and inhibit platelet aggregation in humans (Keen et al. (2005) Am J Clin Nutr 81 (1 Suppl): 298S-303S; Vita J A (2005) Am J Clin Nutr 81 (Suppl): 292S-7S; Heptinstall et al. (2006) J Cardiovasc Pharmacol 47 Suppl 2: S197-205).

Thus, according to a further aspect, there is provided a polyphenol extract as hereinbefore defined for use in the prophylaxis or treatment of cardiovascular disease or colon cancer.

In a further aspect, there is provided a use of a polyphenol extract as hereinbefore defined in the manufacture of a medicament for use in the prophylaxis or treatment of cardiovascular disease or colon cancer.

In a yet further aspect of the invention there is provided a method of treatment or prophylaxis of cardiovascular disease or colon cancer, which comprises administration of a polyphenol extract as hereinbefore defined.

In a yet further aspect of the invention there is provided a pharmaceutical composition comprising a polyphenol extract for use in the prophylaxis or treatment of cardiovascular disease or colon cancer.

According to a further aspect of the invention, there is provided a polyphenol extract comprising one or more low molecular weight polyphenols for use in the prophylaxis or treatment of cardiovascular disease.

In a further aspect, there is provided a use of a polyphenol extract comprising one or more low molecular weight polyphenols in the manufacture of a medicament for use in the prophylaxis or treatment of cardiovascular disease.

In a yet further aspect of the invention there is provided a method of treatment or prophylaxis of cardiovascular disease, which comprises administration of a polyphenol extract comprising one or more low molecular weight polyphenols.

In a yet further aspect of the invention there is provided a pharmaceutical composition comprising a polyphenol extract comprising one or more low molecular weight polyphenols for use in the prophylaxis or treatment of cardiovascular disease.

In a further aspect, there is provided a polyphenol extract comprising one or more high molecular weight polyphenols for use in the prophylaxis or treatment of colon cancer.

In a further aspect, there is provided a use of a polyphenol extract comprising one or more high molecular weight polyphenols in the manufacture of a medicament for use in the prophylaxis or treatment of colon cancer.

In a yet further aspect of the invention there is provided a method of treatment or prophylaxis of colon cancer, which comprises administration of a polyphenol extract comprising one or more high molecular weight polyphenols.

In a yet further aspect of the invention there is provided a pharmaceutical composition comprising a polyphenol extract comprising one or more high molecular weight polyphenols for use in the prophylaxis or treatment of colon cancer.

It will be appreciated that the term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal, in particular a human being, but it may also include animals, such as dogs, cats, cows, sheep, horses and pigs.

It will also be appreciated that references herein to "polyphenol extract" are intended to include one or more polyphenols extracted from an apple in accordance with the process of the invention. This term is also intended to include isolated polyphenols which may have been purified from the crude extract (e.g. by chromatographic separation).

Combination Therapies

Many diseases are treated using more than one medicament in the treatment, either concomitantly administered or sequentially administered. It is therefore within the scope of the invention to use the polyphenol extracts of the invention in therapeutic methods for the treatment of one of the above mentioned diseases in combination with one another, or as an adjunct to, or in conjunction with, other established therapies normally used to in the treatment said disease. In one embodiment, there is provided a pharmaceutical composition comprising a polyphenol extract as hereinbefore defined in combination with one or more additional therapeutic agent.

By analogy, it is also within the scope of the invention to use the polyphenol extracts of the invention in combination with other therapeutically active compounds normally used in the treatment of one of the above-mentioned diseases in the manufacture of a medicament for said disease.

The combination treatment may be carried out in any way as deemed necessary or convenient by the person skilled in the art and for the purpose of this specification, no limitations with regard to the order, amount, repetition or relative amount of the compounds to be used in combination is contemplated.

Compositions

In one embodiment, the polyphenol extracts obtained by the process of the invention may be used in combination with other prebiotic agents, for example monosaccharides, disaccharides and polysaccharides. Thus, according to a further aspect of the invention, there is provided a prebiotic composition, comprising a polyphenol extract having one or more high molecular weight polyphenols and one or more monosaccharide, disaccharide or polysaccharide. A suitable saccharide is oligofructose which has the structure shown in formula (XI):

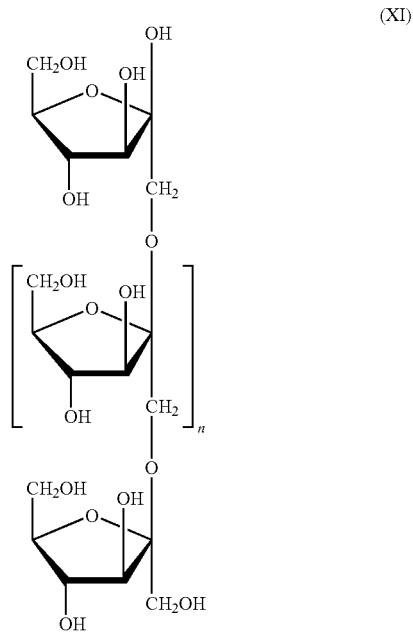

wherein n is typically in the range 2 to 14, suitably 2 to 10, e.g. 2 to 8.

In a further embodiment, the polyphenol extracts of the invention may be used in combination with conventional apple extracts, which provides various monosaccharides, disaccharides and polysaccharides.

When the polyphenols are used in combination with other prebiotic agents or conventional apple extracts, the components may be administered either sequentially or simultaneously by any convenient route. This combination provides the advantage of stimulating the micro flora, which helps to improve gut health, gut function, calcium absorption and immune response, as well as further reducing the risk of colon cancer (Rios, L. et al., supra).

In one aspect, the invention provides a dosage form, which comprises the polyphenol extracts and/or the combinations referred to above (hereinafter referred to as the compositions of the invention).

The compositions of the invention may conveniently be administered alone or in combination with pharmaceutically acceptable carriers or excipients. The compositions of the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water.

Similarly, the carrier or diluent may include any sustained release material known in the art, such as glyceryl monostearate or glyceryl distearate, alone or mixed with a wax. The pharmaceutical compositions formed by combining the compositions of the invention and the pharmaceutically acceptable carriers are then readily administered in a variety of dosage forms suitable for the disclosed routes of administration. The formulations may conveniently be presented in unit dosage form by methods known in the art of pharmacy.

Thus, in a further aspect, there is provided a dosage form comprising a polyphenol extract having one or more low molecular weight polyphenols, or a pharmaceutically acceptable salt, or prodrug thereof, and one or more pharmaceutically acceptable carriers, excipients, or diluents for use in the treatment of cardiovascular disease.

Thus, in a further aspect, there is provided a dosage form comprising a polyphenol extract having one or more high molecular weight polyphenols, or a pharmaceutically acceptable salt, or prodrug thereof, and one or more pharmaceutically acceptable carriers, excipients, or diluents for use in the treatment of colon cancer.

The dosage forms may be formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

For topical use, sprays, creams, ointments, jellies, gels, inhalants, dermal patches, implants, solutions of suspensions, etc., containing the compounds of the present invention are contemplated. For the purpose of this application, topical applications shall include mouthwashes and gargles.

Compositions for oral administration include solid dosage forms, such as hard or soft capsules, tablets, troches, dragees, pills, lozenges, powders, granules, and liquid dosage forms such as solutions, emulsions, aqueous or oily suspensions, syrups and elixirs, each containing a predetermined amount of the compositions of the invention, and which may include a suitable excipient. Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations.

Aqueous suspensions may contain the compositions of the invention in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the compositions of the invention in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the compositions of the invention in admixture with a dispersing or wetting agent, suspending agent and one or more preservatives. Suitable dispersing or wetting agents and suspending agents are exemplified by those already mentioned above. They may also contain buffering agents such as citrate and phosphate buffers, effervescent agents formed from carbonates, e.g. bicarbonates such as sodium or ammonium bicarbonate, and a solic acid, for example citric acid or an acid citrate salt. Additional excipients, for example, sweetening, flavouring, and colouring agents may also be present.

The pharmaceutical compositions of the present invention may also be in the form of oil-in-water emulsions. The oily phase may be a vegetable oil, for example olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

In a further embodiment, the polyphenol extracts can be dried, for example spray-dried or dried under vacuum at a temperature less than 30° C., e.g. less than 20° C. and optionally freeze-dried, and formulated into a solid dosage form.

Tablets may contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc.

The tablets may be uncoated or they may be coated by known techniques to delay disintegration and absorption in the gastrointestinal tract and thereby provide a sustained action over a longer period.

Formulations for oral use may also be presented as hard gelatine capsules where the active ingredient is mixed with an inert solid diluent, for example, calcium carbonate, calcium phosphate or kaolin, or a soft gelatine capsules wherein the active ingredient is mixed with water or an oil medium, for example peanut oil, liquid paraffin, or olive oil.

Dosage forms for parenteral administration include sterile aqueous and non-aqueous injectable solutions, dispersions, suspensions or emulsions as well as sterile powders to be reconstituted in sterile injectable solutions or dispersions prior to use. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art. Depot injectable formulations are also contemplated as being within the scope of the present invention.

The compositions for rectal administration of the compounds may also be in the form of suppositories. These compositions can be prepared by mixing the compositions of the invention with a suitable non-irritating excipient which is solid at ordinary temperatures but liquid at the rectal temperature and will thus melt in the rectum to release the compositions of the invention. Such materials include cocoa butter and polyethylene glycols, for example.

The compounds of the invention, or compositions thereof, will generally be used in an amount effective to achieve the intended result, for example in an amount effective to treat or prevent the particular disease being treated. The compound(s) may be administered therapeutically to achieve therapeutic benefit. By therapeutic benefit is meant eradication or amelioration of the underlying disorder being treated and/or eradication or amelioration of one or more of the systems associated with the underlying disorder. Therapeutic benefit also includes halting or slowing the progression of the disease, regardless of whether improvement is realised.

The exact dosage will depend upon the frequency and mode of administration, the sex, age, weight and general condition of the subject treated, the nature and severity of the condition treated and any concomitant diseases to be treated and other factors evident to those skilled in the art. Determination of the effective dosage is well within the capabilities of those skilled in the art.

When the polyphenol extract is used in combination with a second therapeutic agent active against the same disease state the dose of each compound may differ from that when the compound is used alone. Appropriate doses will be readily appreciated by those skilled in the art.

In a further aspect, the invention provides a dietary composition, e.g. a drink, such as a fruit juice, sports drink, yoghurt drink, a milk drink, tea and the like or a solid foodstuff, e.g. a food snack bar, such as a fruit bar, nut bar and cereal bar, a cereal, a dessert, a chocolate (e.g. milk and dark) bar and the like, which comprises the polyphenol extracts and/or the combinations referred to above.

In one embodiment, the dietary composition may additionally comprise other nutrients, e.g. vitamins, minerals, and prebiotics, such as oligofructose and apple fibres, and probiotics.

In one embodiment, the dietary composition is formulated as a liquid dosage form as hereinbefore defined. In a further embodiment, the liquid dosage form may additionally comprise thickeners, tonicity adjusting agents and buffering agents.

Examples of suitable tonicity adjusting agents include sugars and sodium chloride, which can be used to provide a solution of a particular strength, for example and isotonic solution. Examples of suitable buffering agents include citrates and phosphates.

In a further embodiment, the foodstuff comprises the polyphenol extract as hereinbefore defined. In a further embodiment, the polyphenol extract may be admixed with one or more ingredients, for example dried fruit, nuts and cereals.

Thus, in a further aspect, there is provided a dietary composition as hereinbefore defined comprising a polyphenol extract having one or more low molecular weight polyphenols for use in the prophylaxis or treatment of cardiovascular disease.

In a further aspect, there is provided a dietary composition as hereinbefore defined comprising a polyphenol extract having one or more low molecular weight polyphenols in the manufacture of a medicament for use in the prophylaxis or treatment of cardiovascular disease.

In a yet further aspect of the invention there is provided a method of treatment or prophylaxis of cardiovascular disease, which comprises administration of a dietary composition as hereinbefore defined comprising a polyphenol extract having one or more low molecular weight polyphenols.

Thus, in a further aspect, there is provided a dietary composition as hereinbefore defined comprising a polyphenol extract having one or more high molecular weight polyphenols for use in the prophylaxis or treatment of colon cancer.

In a further aspect, there is provided a dietary composition as hereinbefore defined comprising a polyphenol extract having one or more high molecular weight polyphenols in the manufacture of a medicament for use in the prophylaxis or treatment of colon cancer.

In a yet further aspect of the invention there is provided a method of treatment or prophylaxis of colon cancer, which comprises administration of a dietary composition as hereinbefore defined comprising a polyphenol extract having one or more high molecular weight polyphenols.

The invention will now be illustrated by the following non-limiting Examples.

EXAMPLES

General Procedures

Figure 1:
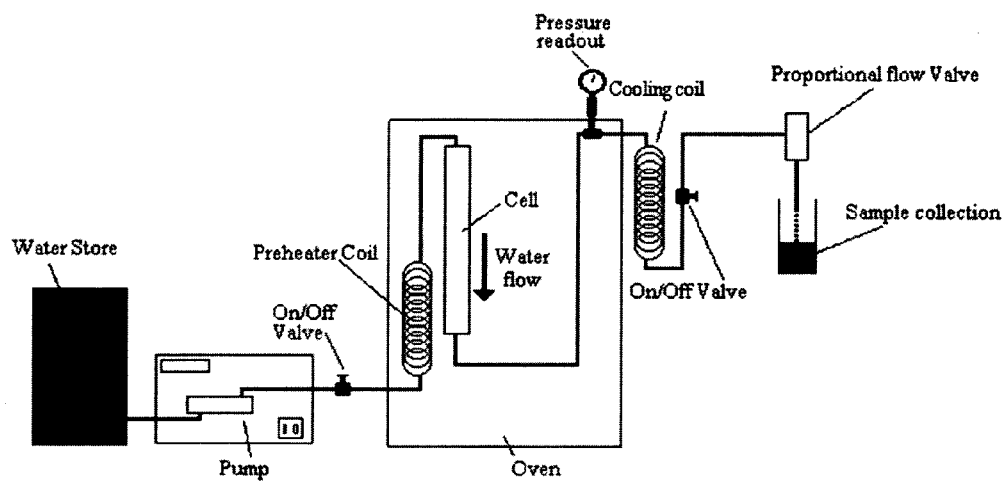
FIG. 1 demonstrates a schematic arrangement of the process of the invention.

Approximately 6 g of freeze-dried apple was weighed into a beaker and the weight recorded. To this 15 ml of deionised, distilled, degassed water is added to form a thick paste, which is then transferred to an extraction cell which has been part filled with deionised and deaerated water. The remaining cell volume was filled with water, sealed and placed into the oven of the extraction system (which is shown in FIG. 1). Water was pumped in until a stable pressure of approx 4 bar was achieved. The oven was then set to the desired temperature and allowed to equilibrate for 30 minutes prior to the start of the sample collection phase.

After 30 minutes with water flow at a fixed rate, samples were collected over a two-hour period, which were sampled and analysed by HPLC. The concentration of (−)-epicatechin in solution was then calculated and used to assess the rate of extraction over a range of temperatures.

HPLC Method

Column: Waters RP18 ($C_{18}$ stationary phase 4.6×150 mm, 3.5 µm particle size)

Grad column: Waters RP18 (4.6×50 mm, 3.5 µm particle size)

Oven temperature: 30° C.

Binary mobile phase: Component A. Water containing 2% acetic acid.

Component B. Methanol containing 0.1% acetic acid

TABLE 1

Gradient elution profile

| Gradient type | % A | % B | Elapsed time (min) |
|---|---|---|---|
| Initial | 85 | 15 | 0 |
| Linear | 55 | 45 | 25 |
| Linear | 15 | 85 | 26 |
| Hold | 15 | 85 | 35 |
| Linear | 85 | 15 | 37 |
| Hold | 85 | 15 | 40 |
| Post run time | 85 | 15 | 5 |

Example 1

Effect of Solvent Extraction Temperature upon Epicatechin Extraction

The extraction analysis was performed on 6 different temperatures as shown in Table 2.

TABLE 2

Extraction Conditions

| Test I.D. | Temperature (° C.) | Water flow rate (ml/min) |
|---|---|---|
| A | 20 (Ambient) | 100 ml static volume |
| B | 50 | 1.0 |
| C | 75 | 1.0 |
| D | 100 | 1.0 |
| E | 125 | 1.0 |
| F | 150 | 1.0 |

(A) Extraction at 20° C.

Figure 2:
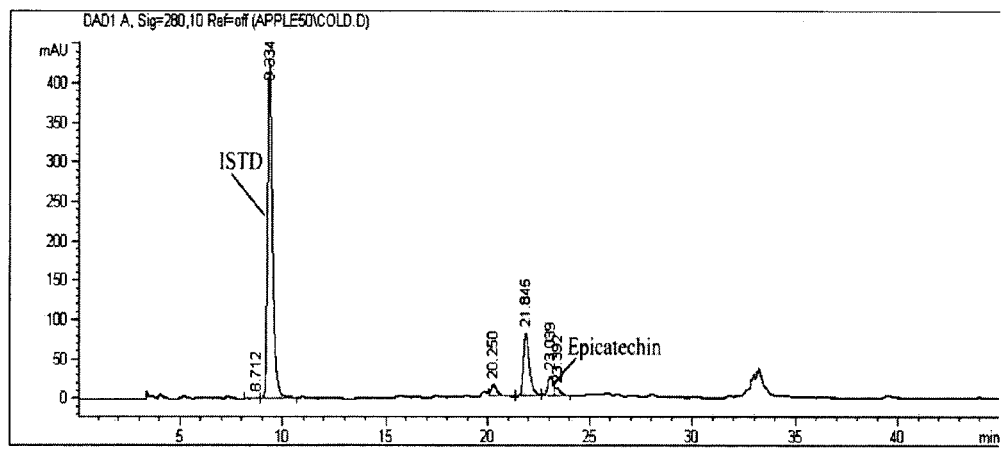
FIGS. 2-13 demonstrate the results of the analysis of the effect of solvent extraction temperature upon epicatechin extraction.

10.001 g of apple powder were placed in a beaker with 100 ml water, mixed well covered with sealing film and left for 2 hours. 1 ml of the resulting solution was then filtered through a 0.45 µm syringe filter into a 2 ml auto sampler vial to which was added 50 µl of internal standard solution of epicatechin (obtained from Sigma). The results of the chromatography are shown in FIG. 2 and once analysed the solution gave rise to a concentration of 825.28 mg epicatechin/Kg of apple powder.

(B) Extraction at 50° C.

6.137 g of apple powder were extracted in accordance with the "General Procedures" previously described. 1 ml of each of the resulting solutions was then filtered through a 0.45 µm syringe filter into a 2 ml auto sampler vial to which was added 50 µl of internal standard solution of epicatechin (obtained from Sigma). The results are presented in Table 3.

TABLE 3

Results of 50° C. Extraction

| Extract vol (ml) | (−)-epicatechin (mg) in volume | Total (−)-epicatechin extracted (mg) | % cumul (−)-epicatechin |
|---|---|---|---|
| 10 | 0.247 | 0.247 | 2.0 |
| 15 | 0.062 | 0.308 | 2.5 |
| 25 | 0.577 | 0.885 | 7.2 |
| 35 | 4.597 | 5.482 | 44.5 |
| 45 | 1.498 | 6.980 | 56.6 |
| 55 | 2.554 | 9.534 | 77.4 |
| 65 | 1.607 | 11.141 | 90.4 |
| 75 | 0.689 | 11.830 | 96.0 |
| 85 | 0.287 | 12.117 | 98.3 |
| 95 | 0.147 | 12.264 | 99.5 |
| 105 | 0.058 | 12.322 | 100.0 |
| 110 | 0.000 | 12.322 | 100.0 |

Figure 3:
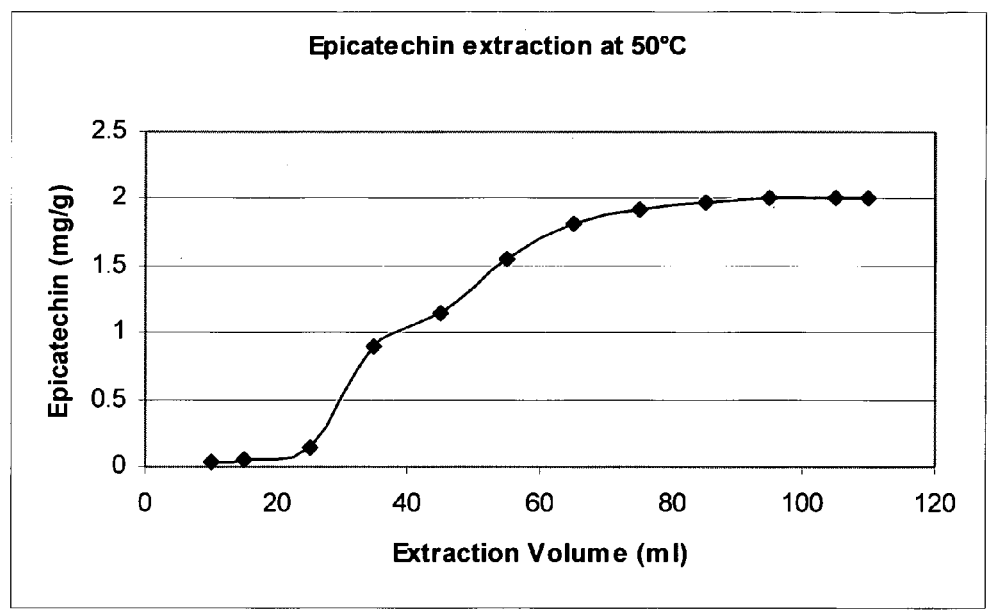
Figure 4:
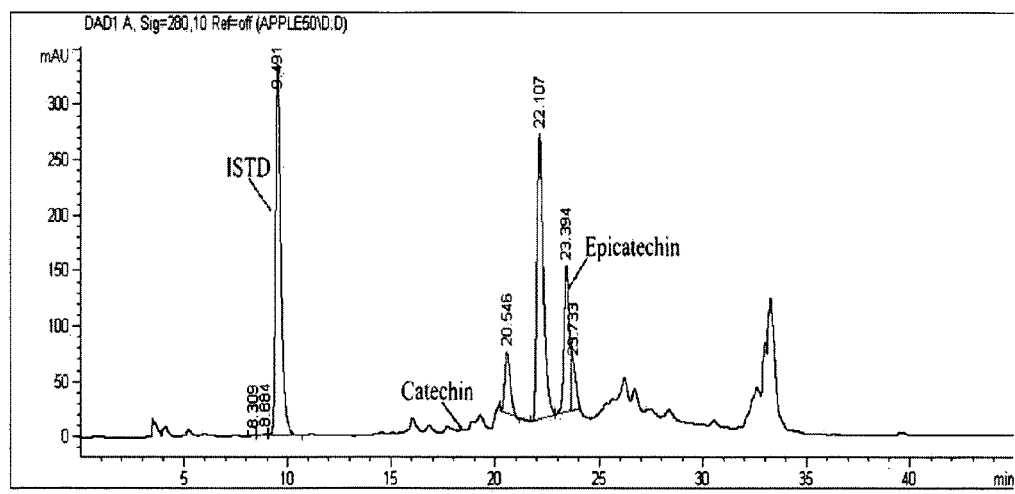

The cumulative results of the 50° C. extraction are shown in FIG. 3 and the results of the chromatography are shown in FIG. 4.

The results of this analysis obtained 2.01 mg of epicatechin per gram of apple powder (equivalent to 2007.85 mg/kg):

| | Sample (g) | mg/g | mg/kg |
|---|---|---|---|
| 50° C. | 6.137 | 2.01 | 2007.85 |

(C) Extraction at 75° C.

6.595 g of apple powder were extracted in accordance with the "General Procedures" previously described. 1 ml of each of the resulting solutions was then filtered through a 0.45 µm syringe filter into a 2 ml auto sampler vial to which was added 50 µl of internal standard solution of epicatechin (obtained from Sigma). The results are presented in Table 4.

TABLE 4

Results of 75° C. Extraction

| Extract vol (ml) | (−)-epicatechin (mg) in volume | Total (−)-epicatechin extracted (mg) | % cumul (−)-epicatechin |
|---|---|---|---|
| 10 | 3.097 | 3.097 | 16.8 |
| 20 | 4.926 | 8.023 | 43.6 |
| 30 | 2.981 | 11.004 | 59.8 |

TABLE 4-continued

Results of 75° C. Extraction

| Extract vol (ml) | (−)-epicatechin (mg) in volume | Total (−)-epicatechin extracted (mg) | % cumul (−)-epicatechin |
|---|---|---|---|
| 40 | 2.045 | 13.049 | 70.9 |
| 51 | 1.553 | 14.602 | 79.4 |
| 60 | 1.025 | 15.627 | 84.9 |
| 70 | 0.841 | 16.468 | 89.5 |
| 80 | 0.683 | 17.151 | 93.2 |
| 93 | 0.663 | 17.814 | 96.8 |
| 100 | 0.233 | 18.047 | 98.1 |
| 110 | 0.222 | 18.270 | 99.3 |
| 120 | 0.131 | 18.400 | 100.0 |

Figure 5:
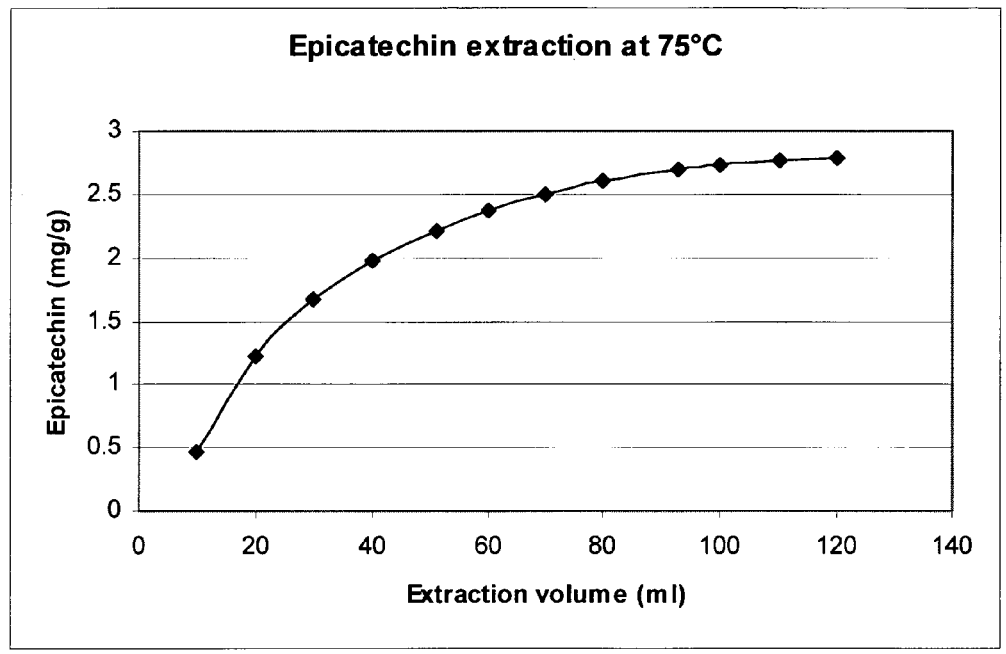
Figure 6:
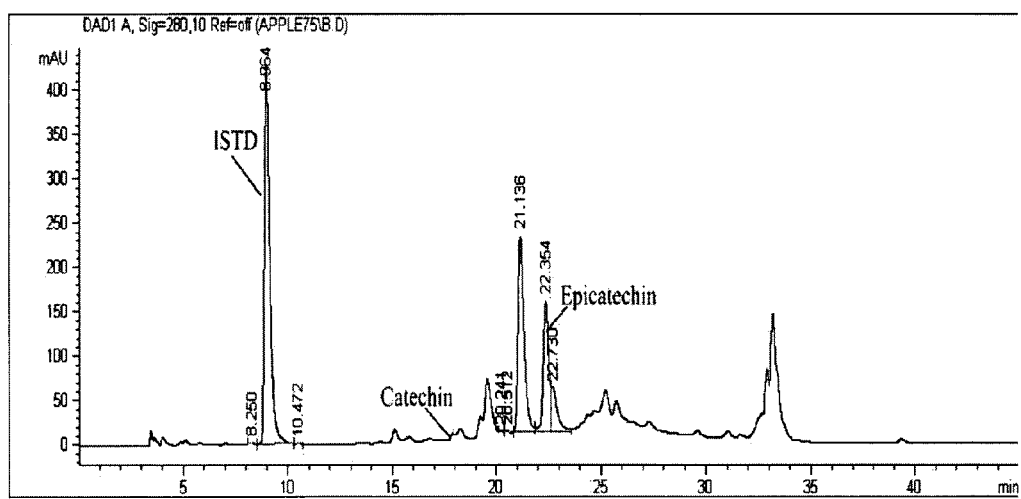

The cumulative results of the 75° C. extraction are shown in FIG. 5 and the results of the chromatography are shown in FIG. 6.

The results of this analysis obtained 2.79 mg of epicatechin per gram of apple powder (equivalent to 2790.02 mg/kg):

| | Sample (g) | mg/g | mg/kg |
|---|---|---|---|
| 75° C. | 6.595 | 2.79 | 2790.02 |

(D) Extraction at 100° C.

6.0962 g of apple powder were extracted in accordance with the "General Procedures" previously described. 1 ml of each of the resulting solutions was then filtered through a 0.45 µm syringe filter into a 2 ml auto sampler vial to which was added 50 µl of internal standard solution of epicatechin (obtained from Sigma). The results are presented in Table 5.

TABLE 5

Results of 100° C. Extraction

| Extract vol (ml) | (−)-epicatechin (mg) in volume | Total (−)-epicatechin extracted (mg) | % cumul (−)-epicatechin |
|---|---|---|---|
| 11 | 1.126 | 1.126 | 6.9 |
| 21 | 4.089 | 5.215 | 31.9 |
| 31 | 3.819 | 9.034 | 55.3 |
| 41 | 2.806 | 11.840 | 72.5 |
| 52 | 1.884 | 13.724 | 84.0 |
| 61 | 1.087 | 14.811 | 90.6 |
| 71 | 0.670 | 15.481 | 94.7 |
| 81 | 0.429 | 15.910 | 97.4 |
| 91 | 0.214 | 16.123 | 98.7 |
| 102 | 0.162 | 16.285 | 99.7 |
| 111 | 0.057 | 16.342 | 100.0 |
| 121 | 0.000 | 16.342 | 100.0 |
| 161 | 0.000 | 16.342 | 100.0 |

Figure 7:
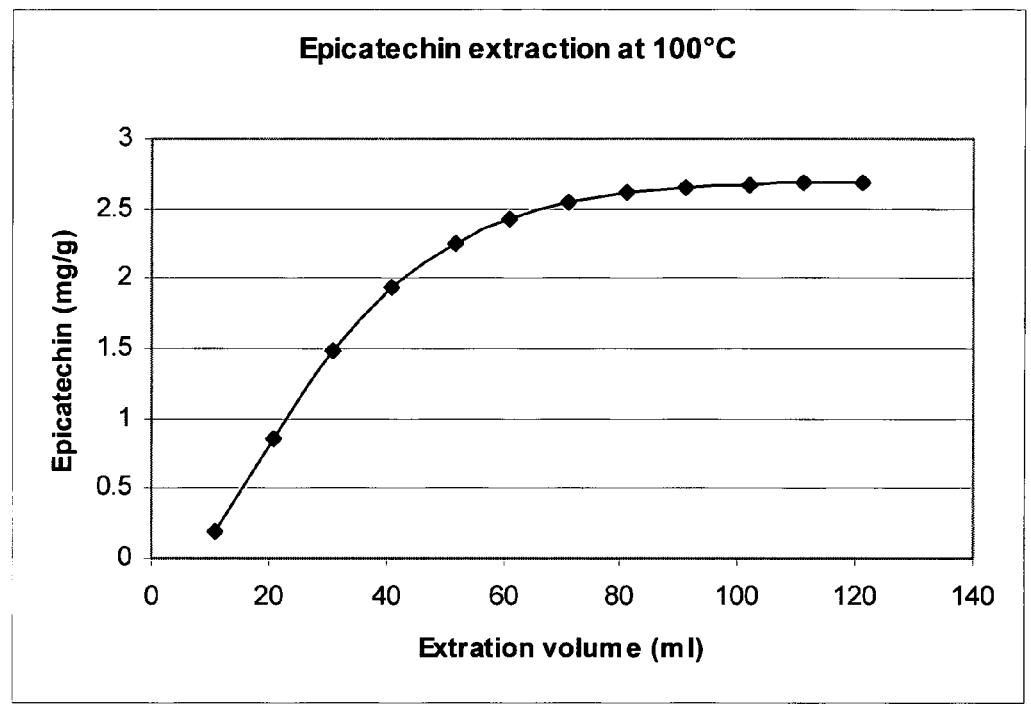
Figure 8:
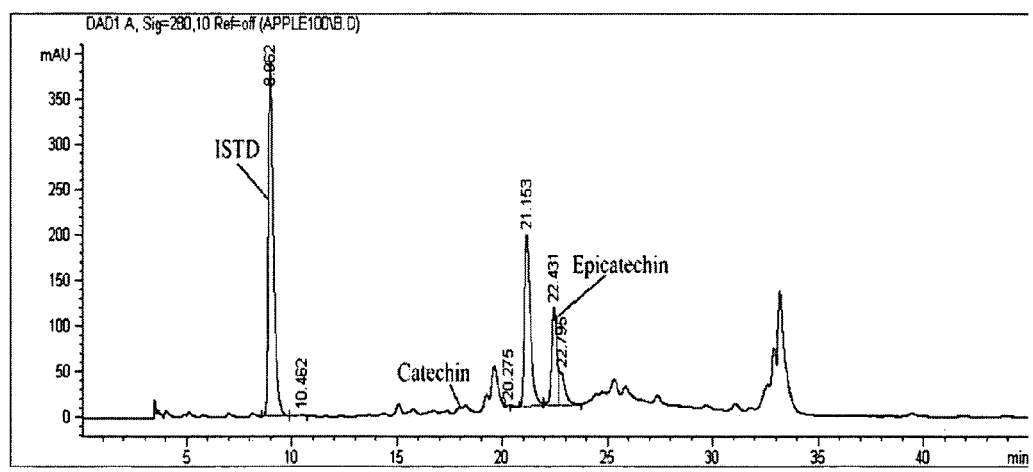

The cumulative results of the 100° C. extraction are shown in FIG. 7 and the results of the chromatography are shown in FIG. 8.

The results of this analysis obtained 2.68 mg of epicatechin per gram of apple powder (equivalent to 2680.71 mg/kg):

| | Sample (g) | mg/g | mg/kg |
|---|---|---|---|
| 100° C. | 6.0962 | 2.68 | 2680.71 |

(E) Extraction at 125° C.

6.2038 g of apple powder were extracted in accordance with the "General Procedures" previously described. 1 ml of each of the resulting solutions was then filtered through a 0.45 µm syringe filter into a 2 ml auto sampler vial to which was added 50 µl of internal standard solution of epicatechin (obtained from Sigma). The results are presented in Table 6.

TABLE 6

Results of 125° C. Extraction

| Extract vol (ml) | (−)-epicatechin (mg) in volume | Total (−)-epicatechin extracted (mg) | % cumul (−)-epicatechin |
|---|---|---|---|
| 15 | 4.003 | 4.003 | 31.2 |
| 25 | 4.505 | 8.508 | 66.2 |
| 35 | 1.910 | 10.418 | 81.1 |
| 45 | 1.130 | 11.549 | 89.9 |
| 55 | 0.513 | 12.061 | 93.9 |
| 65 | 0.305 | 12.367 | 96.3 |
| 75 | 0.173 | 12.540 | 97.6 |
| 85 | 0.099 | 12.639 | 98.4 |
| 95 | 0.087 | 12.725 | 99.1 |
| 106 | 0.056 | 12.781 | 99.5 |
| 115 | 0.032 | 12.813 | 99.8 |
| 125 | 0.030 | 12.843 | 100.0 |
| 165 | 0.000 | 12.843 | 100.0 |

Figure 9:
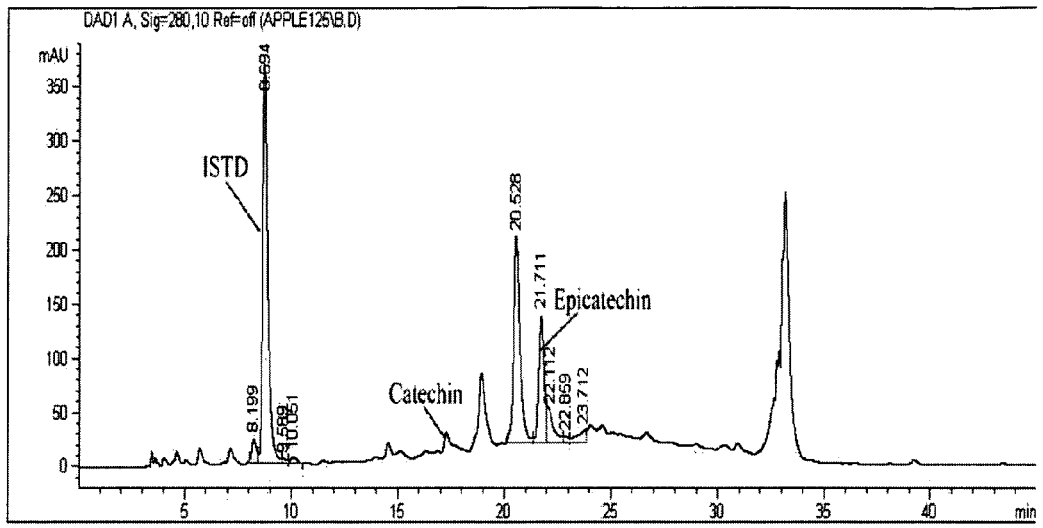

The results of the chromatography are shown in FIG. 9.

The results of this analysis obtained 2.07 mg of epicatechin per gram of apple powder (equivalent to 2070.21 mg/kg):

| | sample (g) | mg/g | mg/kg |
|---|---|---|---|
| 125° C. | 6.2038 | 2.07 | 2070.21 |

(F) Extraction at 150° C.

6.6651 g of apple powder were extracted in accordance with the "General Procedures" previously described. 1 ml of each of the resulting solutions was then filtered through a 0.45 µm syringe filter into a 2 ml auto sampler vial to which was added 50 µl of internal standard solution of epicatechin (obtained from Sigma). The results are presented in Table 7.

TABLE 7

Results of 150° C. Extraction

| Extract vol (ml) | (−)-epicatechin (mg) in volume | Total (−)-epicatechin extracted (mg) | % cumul (−)-epicatechin |
|---|---|---|---|
| 16 | 1.061 | 1.061 | 42.9 |
| 29 | 0.901 | 1.962 | 79.4 |
| 39 | 0.245 | 2.208 | 89.3 |
| 49 | 0.120 | 2.327 | 94.1 |
| 59 | 0.101 | 2.429 | 98.2 |
| 69 | 0.044 | 2.473 | 100.0 |
| 79 | 0.000 | 2.473 | 100.0 |
| 93 | 0.000 | 2.473 | 100.0 |
| 103 | 0.000 | 2.473 | 100.0 |
| 116 | 0.000 | 2.473 | 100.0 |
| 126 | 0.000 | 2.473 | 100.0 |
| 136 | 0.000 | 2.473 | 100.0 |

Figure 10:
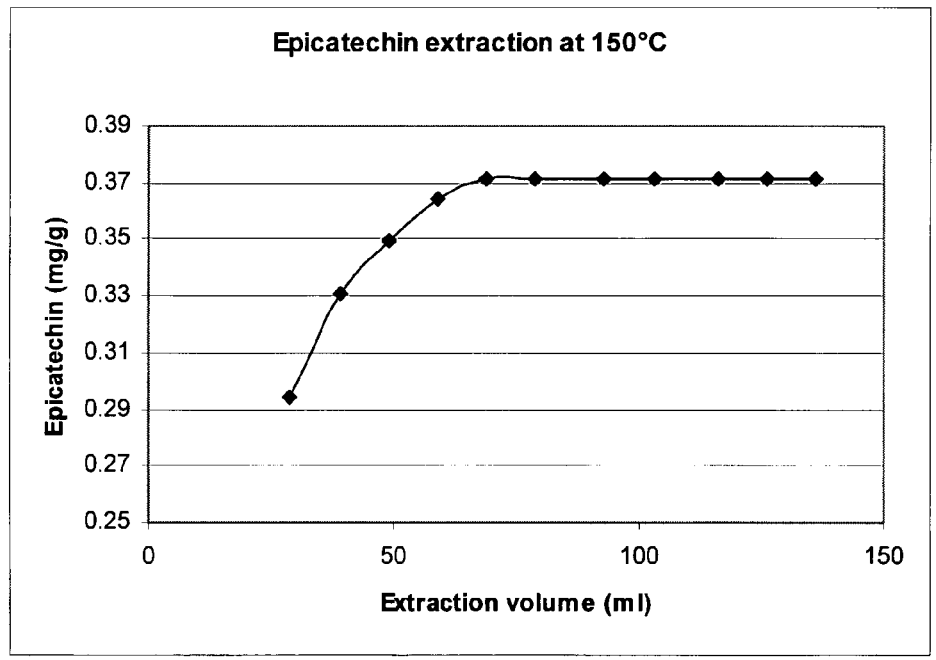
Figure 11:
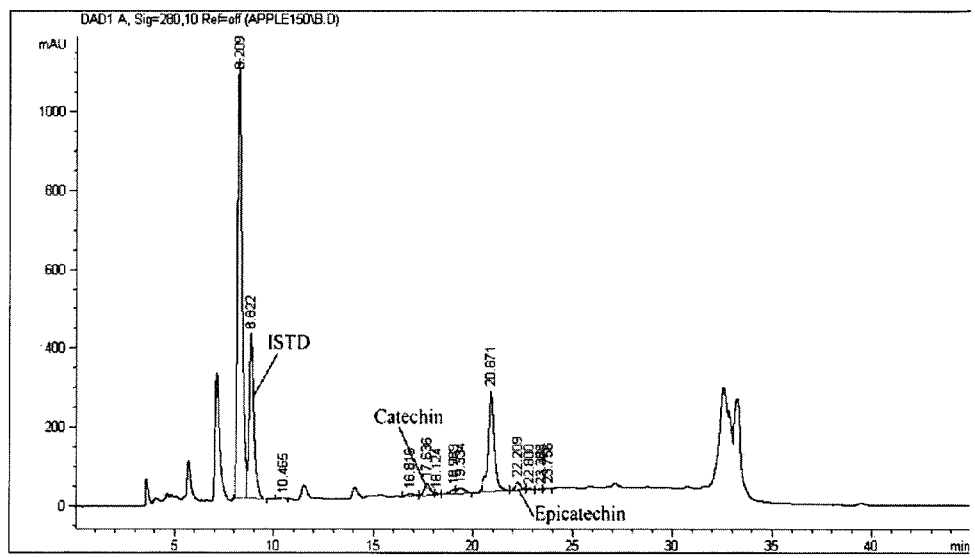

The cumulative results of the 100° C. extraction are shown in FIG. 10 and the results of the chromatography are shown in FIG. 11.

The results of this analysis obtained 0.37 mg of epicatechin per gram of apple powder (equivalent to 371.00 mg/kg):

| | sample (g) | mg/g | mg/kg |
|---|---|---|---|
| 150° C. | 6.6651 | 0.37 | 371.00 |

(G) Summary of Results

Figure 12:
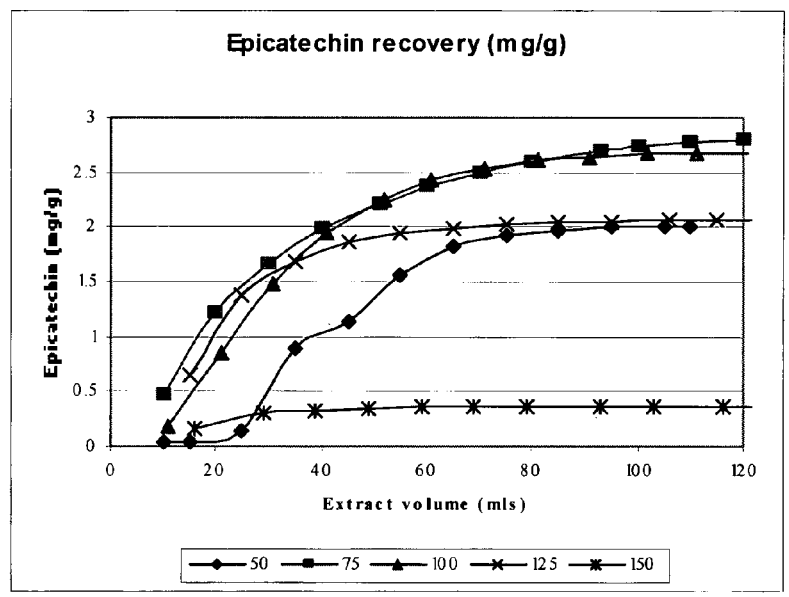
Figure 13:
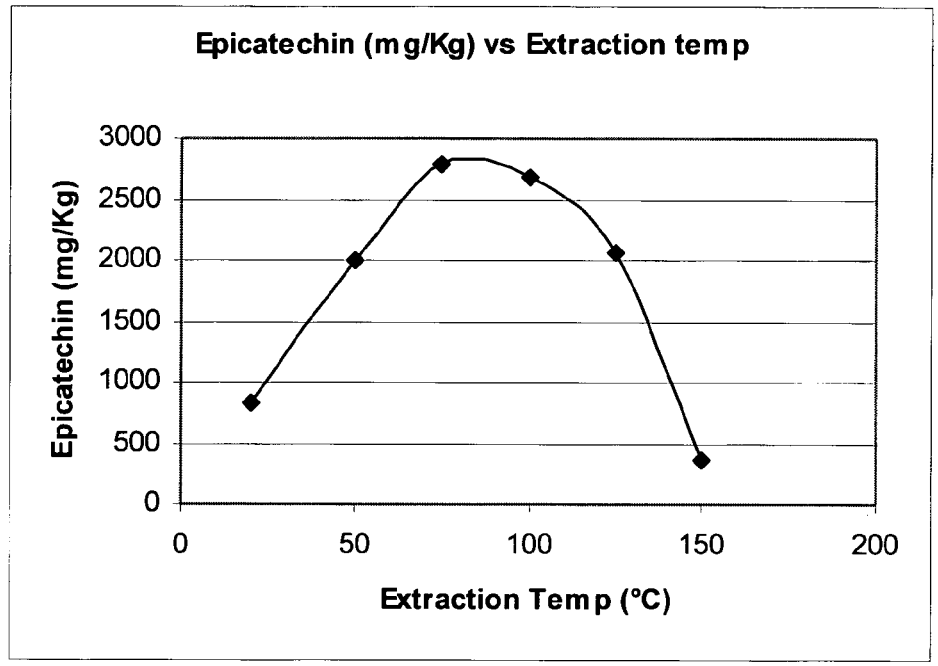

The data obtained from each of extractions (A)-(F) were overlaid and are shown in FIG. 12 which demonstrates a comparison in apparent extraction rate at a given temperature. FIG. 13 shows the effectiveness of each of the extraction temperatures for extraction of epicatechin (peak effectiveness was shown to be 83%). From FIG. 13 it can be seen that above 75° C., the overall concentration of epicatechin extracted falls. It is possible that the reduced effectiveness may be caused by isomerisation (epimerisation) of epicatechin to catechin at higher temperatures.

Example 2

Detection of Catechin in Extracts

In order to test the possibility that epicatechin was isomerising to catechin at higher temperatures, a test solution of 0.688 mg/ml epicatechin was produced and treated as follows: 950 µl of epicatechin was transferred to an auto sampler vial, which was flushed with nitrogen and sealed. The vial was then placed in an oven at a given temperature, for a set time period. The vial was then cooled, the seal removed and 50 µl of internal standard added before analysis. Tests were carried out at 50, 75, 100 and 125° C. for 15 and 30 minutes. Tests were not carried out at 150° C. as the vials are not capable of withstanding the pressure that would be generated.

The concentrations of epicatechin and catechin were determined for each test solution and are shown in Table 8.

TABLE 8

(−)-Epicatechin isomerisation results

| | Epicatechin | | Catechin | | Other* | |
|---|---|---|---|---|---|---|
| | mg/ml | % remain | mg/ml | % of start | Other | % of start |
| Start | 0.688 | 100.00 | 0.000 | 0.00 | 0.000 | 0.00 |
| 50° C. 15 min | 0.643 | 93.53 | 0.007 | 1.07 | 0.037 | 5.40 |
| 50° C. 30 min | 0.601 | 87.40 | 0.012 | 1.81 | 0.074 | 10.79 |
| 75° C. 15 min | 0.550 | 79.92 | 0.065 | 9.49 | 0.073 | 10.59 |
| 75° C. 30 min | 0.441 | 64.07 | 0.112 | 16.28 | 0.135 | 19.65 |
| 100° C. 15 min | 0.254 | 36.97 | 0.321 | 46.68 | 0.113 | 16.36 |
| 100° C. 30 min | 0.164 | 23.88 | 0.344 | 50.05 | 0.179 | 26.07 |
| 125° C. 15 min | 0.156 | 22.71 | 0.340 | 49.36 | 0.192 | 27.94 |
| 125° C. 30 min | 0.139 | 20.27 | 0.300 | 43.60 | 0.249 | 36.13 |

*note calculated from 100 − (epicatechin + catechin).

The rapid isomerisation of (−)-epicatechin at temperatures above 100° C. indicated that these temperatures are unsuitable for further study, and that the overall time at which the sample is kept at elevated temperatures should be maintained as short as possible.

Example 3

Methanol Extraction Analysis

Triplicate extractions were performed with methanol on approximately 1 g of apple powder extracted in accordance with the "General Procedures" previously described. The apple sample was weighed into a 60 ml centrifuge tube and 25 ml of methanol added. The samples were shaken and placed in an oven set at 55° C. for 20 minutes and allowed to extract, the samples were re-shaken every 5 minutes in order to maximise contact. Once extracted the samples were removed from the oven and allowed to cool for 30 minutes. 1 ml of each solution was then filtered through a 0.45 µm syringe filter into a 2 ml auto sampler vial to which was added 50 µl of internal standard solution. The results are demonstrated in Table 9.

TABLE 9

Results of Methanol Extraction

| Sample | mg/ml | Vol | mg in tot vol |
|---|---|---|---|
| Meth 1 | 0.32 | 25 | 8.01 |
| Meth 2 | 0.35 | 25 | 8.73 |
| Meth 3 | 0.38 | 25 | 9.58 |
|  |  | Average | 8.77 |

| | sample (g) | mg/g | mg/kg |
|---|---|---|---|
| Meth 1 | 2.0034 | 4.00 | 4000.29 |
| Meth 2 | 2.0443 | 4.27 | 4269.64 |
| Meth 3 | 2.2301 | 4.30 | 4295.73 |
|  |  | Average | 4188.55 |

Figure 14:
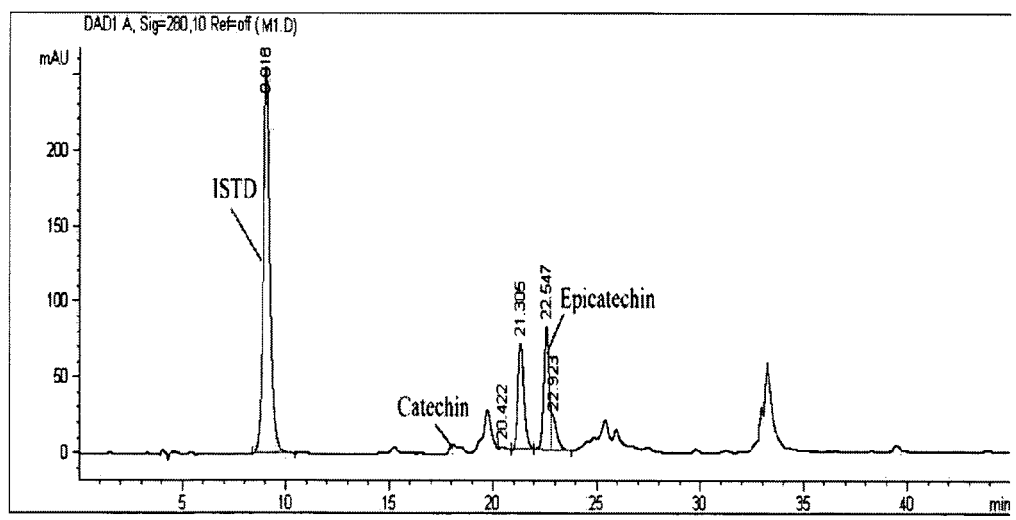
FIGS. 14-15 demonstrate the results of the methanol extraction analysis.

The results of the chromatography are shown in FIG. 14.

Figure 15:
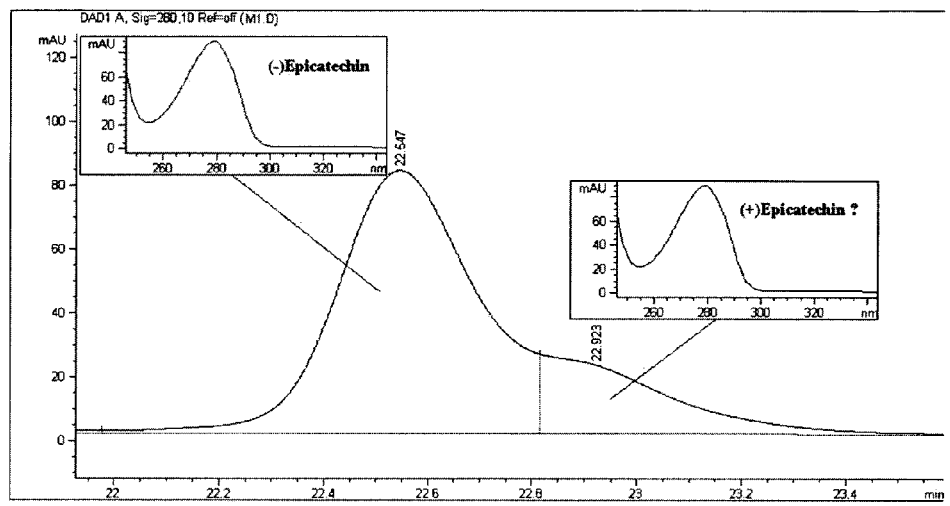

The spectra of the (−)-epicatechin peak obtained in FIG. 14 was examined in order to determine if there was any co-elution of other substances which were not picked up at the data collection wavelength of 280+/−10 nm. The amplification of this peak is shown in FIG. 15. The two spectra were found to be identical to that produced by the (−) epicatechin standard used for quantification. This suggests that the main peak and shoulder are composed of very similar materials, which is evidence that the shoulder may be the (+) isomer of epicatechin. The lack of other traces in the spectra indicated that no other materials are co-eluting at this point in the chromatogram.

Example 4

Isolation of Polyphenols by Chromatography

Small-scale tests were performed using C18-E SPE material and two commercially available ion exchange resins, Amberlite XAD-16 and Purolite MN100.

A test solution containing 9.18 mg of epicatechin in 10 mls of water (0.918 mg/ml) was applied to columns containing 1 g of each of the three test sorbents. The water post treatment was assessed for the presence of epicatechin and it was found that the XAD16 contained 0.261 mg/ml meaning that out of the total applied to the column only 71.6% had been retained. The MN100 and C18 showed no epicatechin present in the treated water. Each of the test sorbents were then eluted with ethanol and the solvent analysed to determine the amount of epicatechin recovered.

The XAD 16 wash was found to contain 5.22 mg of epicatechin giving a total of 7.83 mg (85.3%) of the total added to the sorbent. Leaving 1.35 mg (16.5%) not recovered.

The MN 100 wash was found to contain 4.37 mg of epicatechin giving a total of 4.37 mg (47.6%) of the total added to the sorbent. Leaving 4.81 mg (52.4%) not recovered.

The C18 wash was found to contain 9.03 mg of epicatechin giving a total of 9.03 mg (98.4%) of the total added to the sorbent. Leaving 0.15 mg (1.6%) not recovered.

From the above it can be seen that either the Amberlite XAD 16 or C18-E can be used, however if the XAD-16 is used it would require a much larger bed volume to achieve the same sample loading characteristics. Based on the above data and in order to maximise product return and sample loading, C18-E was found to have the best characteristics for isolating polyphenols from aqueous solution as shown in Table 10:

TABLE 10

Results of Chromatographic Separation with C18

| C18 test data | Volume (ml) | Conc (mg/ml) | Total (mg) added | Recovery % |
|---|---|---|---|---|
| Feed | 10.0 | 0.918 | 9.18 | |
| Recovered | 3.0 | 3.01 | 9.03 | 98.4 |

Figure 16:
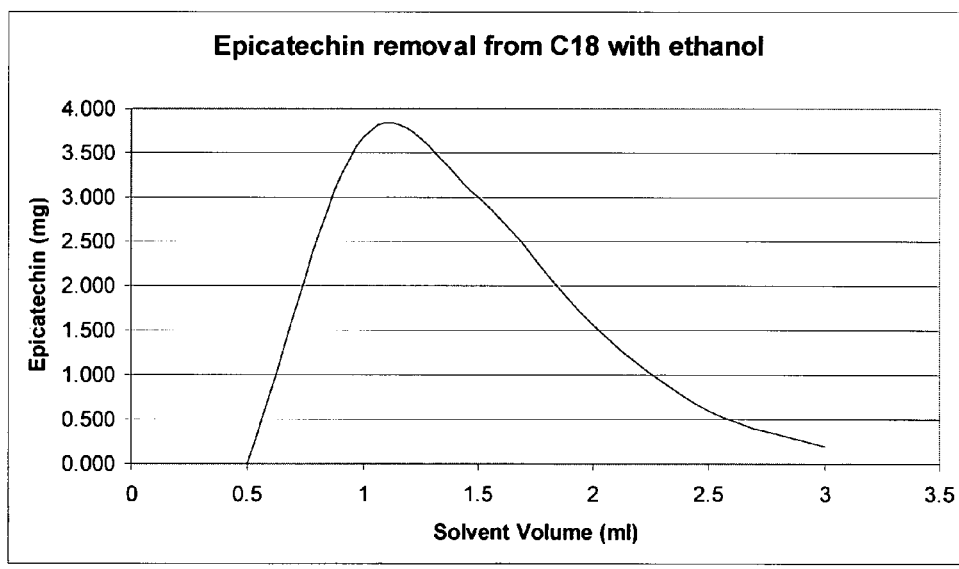
FIG. 16 demonstrates the results of the ethanol extraction analysis.

The cumulative results of the extraction with C18 can be seen in FIG. 16.

Example 5

Ethanol Extraction Analysis

Seven portions of apple powder (approx 50 g) were extracted at a ratio of 4:1 with ethanol at 50° C. The resulting collected ethanol was filtered through a glass fibre filter before being evaporated to collect any solid material available. In total, 377.3 g of apple powder was extracted using 1505 g of ethanol, a ratio of 4:1.

During the evaporation process a quantity of solid material was seen to fall out of solution, this material was recovered by centrifuging the solution. The material collected, 14.6 g of a white sticky solid was analysed and found to contain minute traces of polyphenols, which are probably the result of traces of ethanol trapped in the material.

The remainder of the ethanol was recovered under vacuum at 60° C. and a sticky red semi solid material was recovered weighing 28.9 g. This material was not as expected, a powdery solid. It was probable that this final evaporate contained residues of ethanol, some water, lipids and proteins along with the polyphenols. In order to remove these unwanted substances from the phenols this solid was re-dissolved in water so that it could be passed through a C18-E SPE tube to recover the polyphenol rich fraction.

When the final evaporate was dissolved in water, a layer of non soluble material was seen, when filtered and dried, this material was found to be a solid that contained trace levels of phenols. When the water extract had been passed through the C18-E, the water was analysed and found to contain no epicatechin. The C18-E was eluted with four times the bed volume of ethanol. The ethanol once evaporated gave rise to 1.976 g of red powder, which when analysed was found to contain 18.3% epicatechin.

As the extract had been manipulated many times during the process to get to the powder it was decided to repeat the process without collecting different fractions and proceed as directly as possible to product collection.

The following process was therefore conducted:
1). 338 g of freeze dried apple powder was placed in a 2.5 L glass bottle and extracted with 1045 g of ethanol (ratio of 3:1) for 15 minutes at 60° C.
2). The resulting mixture was hot filtered by vacuum and the ethanol recovered. The apple powder, which still contained some ethanol, was placed back into the extraction bottle and sealed.

3). The collected extract was evaporated by 50% and any non-soluble material removed.
4). The remaining volume was further reduced the to around 15% of the initial level for overnight storage.
5). The recovered ethanol was then added back to the apple powder for re-extraction overnight at ambient again the ratio was 3:1.
6). Following overnight soaking, steps 2 to 4 were repeated.
7). The two concentrated ethanol extracts were combined and evaporated until a sticky red semi-solid was produced.
8). 400 ml of hot (50° C.) de-aerated water was added to the sticky solid to dissolve the polyphenols.
9). The aqueous solution was cooled and filtered to remove any non-soluble material (fats).
10). Four, C18-E, 20 g giga tubes were prepared in accordance with the manufacturers instructions prior to use. The C18 bed was first wetted with ethanol then exchanged with four times the bed volume, 240 ml of water to condition the sorbent.
11). The aqueous solution was processed through the C18 tubes to remove the polyphenol rich fraction from solution before washing the bed with water to remove any non bound material.
12). The sorbent bed was then eluted with 240 ml of ethanol, and collected.
13). The ethanol was evaporated to dryness and the solid "powder" collected.
14). A sample of between 2 and 5 mg was analysed for its epicatechin content.

From the initial 338 g of apple powder processed a total of 6.757 g of red powder was obtained which has an epicatechin content of 12.1%. The solids recovered represent 2% of the initial apple powder mass. When equated to a mg/Kg equivalent of dry apple powder the recovered solids give a figure of 2427.1 mg/Kg.

A comparative extract using 1 g of apple powder and 10 ml methanol gave a figure of 4663 mg/Kg. In order to test if the low recovery figure above was due to low solubility of epicatechin in ethanol a series of tests were performed using 10, 20 and 30:1 w/w. The results of which can be seen in Table 11:

TABLE 11

Comparison of ethanol extraction with methanol

| Sample | mg/ml | mls | total mg | Sample | mg/g | mg/kg |
|---|---|---|---|---|---|---|
| Methanol | 0.52 | 10 | 5.20 | 1.115 | 4.66 | 4663.7 |
| Ethanol 10 ml | 0.345 | 10 | 3.45 | 1.206 | 2.86 | 2862.4 |
| Ethanol 20 ml | 0.244 | 20 | 4.87 | 1.029 | 4.74 | 4736.3 |
| Ethanol 30 ml | 0.210 | 30 | 6.31 | 1.241 | 5.09 | 5085.5 |

The data in Table 11 implies that epicatechin has a lower solubility in ethanol than in methanol, but by increasing the ratio comparable solubility's and hence higher yields can be achieved.

Example 6

Cardiovascular Study with Epicatechin Extracts 10 healthy volunteers were recruited to test the effectiveness of the epicatechin extract obtained from the process of the invention as a means of improving the vascular tone and therefore cardiovascular function. 5 volunteers were given a placebo fruit drink and 5 volunteers were provided with the same test drink, but with 1 mg/kg body weight (based on (−)-epicatechin units) added. Vascular tone was continuously quantified by the reflective index obtained by non-invasive digital photoplethysmography and an algorithm for continuous, investigator-independent, automatic analysis of digital volume pulse. The data were presented as relative Stiffness Index SI (m/s) and correlated with vascular age. Pulse waves were measured by the transmission of red and infrared light through the finger pulp. The local minimum of the first derivative was determined and the corresponding turning point (=inflection point) of the pulse wave was thereby defined. The reflective index was calculated from the mean of the third to the seventh data point after the turning point (=inflection point).

Figure 17:
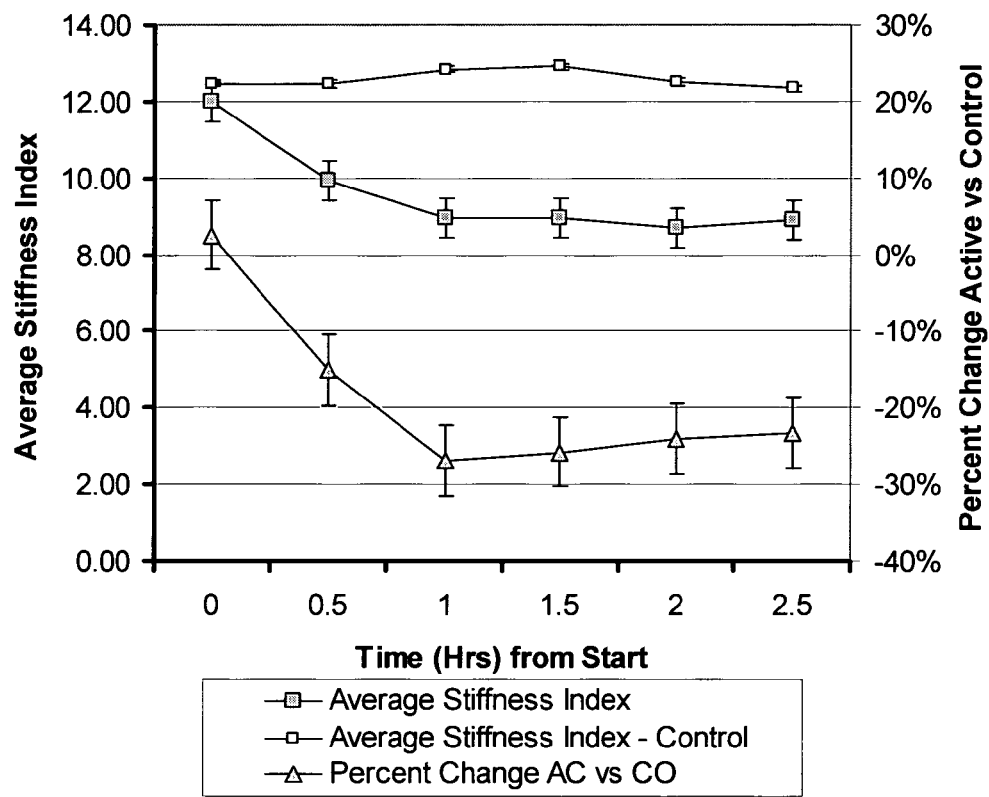
FIGS. 17 and 18 demonstrate the results of the cardiovascular study with epicatechin extracts.
Figure 18:
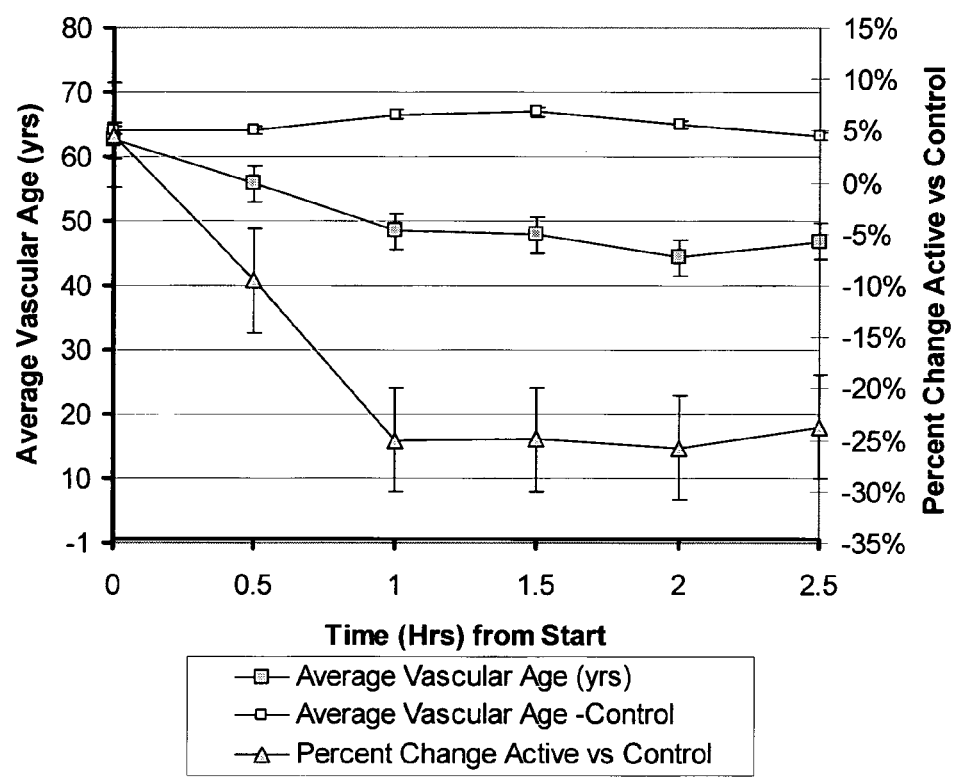

FIGS. 17 and 18 show the results of a 2.5 hour trial. These figures indicate that the arterial stiffness index (SI; FIG. 17) and the Vascular Age (FIG. 18) of the group (n=10) consuming the test drink including the extract was statistically improved (i.e. reduced) when compared to the control.

The invention claimed is:

1. A process for isolating one or more polyphenols from an apple which comprises the steps of:
   (a) removing the natural wax coating of the apple;
   (b) freeze-drying or freezing the apple obtained in step (a);
   (c) powdering the freeze-dried or frozen fruit obtained in step (b);
   (d) subjecting the powdered material obtained in step (c) to one or more solvent extraction cycles wherein the solvent is water;
   (e) evaporating the water from step (d) to form a product;
   (f) chromatographically separating isolated polyphenols from the product of step (e) by elution with ethanol; and
   (g) evaporating ethanol to yield the isolated polyphenols.

2. A process as defined in claim 1, wherein the apple is a "red-cut through" apple.

3. A process as defined in claim 1, wherein said one or more polyphenols comprise epicatechin.

4. A process as defined in claim 1, wherein in step (a), a solvent is used to remove said wax coating.

5. A process as defined in claim 4, wherein the solvent is ethanol, methanol, or acetone.

6. A process as defined in claim 1, wherein step (c) comprises powdering in a conventional food processor in the presence of liquid nitrogen.

7. A process as defined in claim 1, wherein the water in step (d) is deaerated water.

8. A process as defined in claim 1, wherein the water in step (d) is heated to a temperature between 65° C. and 80° C.

9. A process as defined in claim 1, wherein the water in step (d) is at a pressure greater than 1 bar and less than or equal to 5 bar.

* * * * *